(12) United States Patent
Francis et al.

(10) Patent No.: US 7,071,336 B2
(45) Date of Patent: Jul. 4, 2006

(54) PROCESS FOR MANUFACTURING OPIOID ANALGESICS

(75) Inventors: Charles Auxilium Francis, Valparaiso, IN (US); Zhaiwei Lin, Indianapolis, IN (US); Christopher Arne Kaldahl, LaPorte, IN (US); Kazimierz Grzegorz Antczak, Culver, IN (US); Vijai Kumar, Morris Plains, NJ (US)

(73) Assignee: Acura Pharmaceuticals, Palatine, IL (US)

( * ) Notice: Subject to any disclaimer, the term of this patent is extended or adjusted under 35 U.S.C. 154(b) by 0 days.

(21) Appl. No.: 10/892,578

(22) Filed: Jul. 16, 2004

(65) Prior Publication Data

US 2005/0038251 A1    Feb. 17, 2005

Related U.S. Application Data

(63) Continuation-in-part of application No. 10/455,202, filed on Jun. 5, 2003, now Pat. No. 6,864,370.

(51) Int. Cl.
*C07D 471/00* (2006.01)

(52) U.S. Cl. ...................................................... 546/45
(58) Field of Classification Search .................. 546/45
See application file for complete search history.

(56) References Cited

U.S. PATENT DOCUMENTS

| 4,045,440 A | 8/1977 | Rapoport et al. |
| 4,472,253 A | 9/1984 | Schwartz |
| 4,795,813 A | 1/1989 | Schwartz |
| 5,112,975 A | 5/1992 | Wallace |
| 6,008,355 A | 12/1999 | Huang et al. |
| 6,067,749 A | 5/2000 | Fist et al. |
| 6,090,943 A | 7/2000 | Mudryk et al. |
| 6,177,567 B1 | 1/2001 | Chiu et al. |

FOREIGN PATENT DOCUMENTS

EP    0 943 617    9/1999

OTHER PUBLICATIONS

Kranig et al., "Optimization of the Synthesis of Oxycodone and 5-Methyloxycodone", Arch. Pharm. Med. Chem. 329, pp. 325-326, 1996.*
Brown I., et al., "Oxidation Products from Codeine," Journal of The Chemical Society, Oct. 1960, pp. 4139-4140.
Coop, A. et al., "A Novel Synthesis of Thebaine from Codeine," Heterocycles, vol. 49 (1998), pp. 43-47.
Hauser, F.M. et al., "Hydroxycodeinone. An Improved Synthesis," Journal of Medicinal Chemistry, vol. 17, No. 10, (1974), p. 1117.
Krasnig, R. et al., "Optimization of the Synthesis of Oxycodone and 5-Methyloxycodone," Arch. Pharm. Pharm. Med. Chem., (1996), pp. 325-326.
Lijima, I et al., "The Oxidation of Thebaine with m-Chloroperbenzoic Acid," Helvetica Chimica Acta, vol. 60- (1977), pp. 2135-2137.
Merck Index, 13th Edition (2001), pp. 1245-1246.

* cited by examiner

*Primary Examiner*—Cecilia J. Tsang
*Assistant Examiner*—Binta Robinson
(74) *Attorney, Agent, or Firm*—Morgan Lewis & Bockius, LLP

(57) ABSTRACT

Oxycodone is manufactured in high yields and with a high purity using a composition including a thebaine component into 14-hydroxycodeinone and then reduction of 14-hydroxycodeinone to oxycodone.

21 Claims, No Drawings

PROCESS FOR MANUFACTURING OPIOID ANALGESICS

STATEMENT OF RELATED CASES

This application is a continuation-in-part of U.S. patent application Ser. No. 10/455,202, filed Jun. 5, 2003 now U.S. Pat. No. 6,864,370.

BACKGROUND OF THE INVENTION

Oxycodone is a well-known narcotic employed for pain management. Page 1245 of the thirteenth edition of the Merck Index states that oxycodone may be prepared ". . . by catalytic reduction of hydroxycodeinone, its oxime, or its bromination products or by reduction of hydroxycodeinone with sodium hydrosulfite."

The prior art describes several methods for preparing oxycodone using codeine or a salt thereof as the starting composition. Codeine along with morphine, thebaine and oripavine may be extracted from poppy straw, as shown in, for example, U.S. Pat. No. 6,067,749 issued May 30, 2000 to Fist et al. Codeine is also readily prepared by the methylation of morphine, which is present in poppy straw in a higher percentage than that of codeine.

U.S. Pat. No. 6,177,567 BI issued Jun. 23, 2001 to Chiu et al., discloses a method for the preparation of oxycodone and salts thereof which involves the oxidation of codeine to codeinone, formation of a dienolsilyl ether congener of codeinone in strong amine base, oxidation of the dienolsilyl ether congener using peracetic acid and hydrogenation of the 14-hydroxycodeinone product.

In an article by Ivor Brown and M. Martin-Smith appearing on pp. 4139–4140 of the *Journal of The Chemical Society* (October, 1960), the authors disclose several methods for the oxidation of codeine to 14-hydroxycodeinone (which may then be reduced to oxycodone) involving the use of oxidants such as manganese dioxide or chromic oxide in acetic acid.

U.S. Pat. No. 6,008,355 issued Dec. 28, 1999 to Huang et al., discloses methods for preparing oxycodone from codeine. In one method, codeine is oxidized to form codeinone and thereafter the codeinone is converted to oxycodone in a two-step, one-pot reaction involving the reaction of codeinone with hydrogen peroxide in water in the presence of an acid at about 15 to about 70° C. to form 14-hydroxycodeinone and then catalytically hydrogenating 14-hydroxycodeinone in its original reaction mixture to form oxycodone.

In a second method disclosed in the '355 patent, codeine is oxidized to form codeinone, codeinone is then reacted with an acylating agent in water or a solubilizing solvent mixture in the presence of an acid at about 15 to about 70° C. to form acyldienolate. The dienolate is then oxidized to 14-hydroxycodeinone and then the 14-hydroxycodeinone is catalytically hydrogenated in its original reaction mixture to form oxycodone.

SUMMARY OF THE INVENTION (In one embodiment of the present invention, a process for the preparation of oxycodone includes the step of direct oxidation of a composition including a thebaine component into 14-hydroxycodeinone, and then the step of mild reduction of 14-hydroxycodeinone to oxycodone.

In one embodiment, the oxycodone is transformed into a salt, e.g., an acid salt, of oxycodone.

In one embodiment, the composition including a thebaine component includes a solution or a suspension of one or more of concentrate of poppy straw, thebaine or a salt of thebaine.

In one embodiment, to perform the step of direct oxidation, an oxidizing agent can be used. In such embodiments that use an oxidizing agent, the oxidizing agent can be one or more of hydrogen peroxide, peracetic acid, 3-chloroperoxybenzoic acid, and potassium peroxymonosulfate.

In another embodiment, a solvent for oxidation can be used. In such embodiments that use a solvent for oxidation, the solvent can be one or more of acetic acid and water; acetic acid and water and inorganic (mineral) acid; formic acid and water; formic acid and water and inorganic (mineral) acid; formic acid and methanol and water; formic acid and isopropanol; and formic acid and water and isopropanol.

In another embodiment, a solvent for hydrogenation can be used. In such embodiments that use a solvent for hydrogenation, the solvent can be one or more of ethyl acetate and chloroform; dioxane and chloroform; methanol and chloroform; and aqueous phosphate buffer and tetrahydrofuran.

DETAILED DESCRIPTION OF THE INVENTION

Certain embodiments of the present invention are related to processes and methods for the production of opioid analgesics, e.g., oxycodone. In one embodiment, the invention includes starting compositions which include thebaine. In another embodiment, the invention includes starting compositions which include codeine, which in certain embodiments, is then chemically converted to compositions including thebaine, and then to oxycodone. Embodiments of the invention are described in more detail hereafter.

A. Starting Compositions Including a Thebaine Component

In one embodiment, the starting composition for carrying out the process of the invention is a composition that includes a "thebaine component." For the purposes of this invention, the term "thebaine component" shall be understood to encompass thebaine itself, a thebaine salt or any material, composition, mixture or formulation that contains thebaine or a thebaine salt such as opium or a concentrate of poppy straw (CPS) or thebaine from any other source. In one embodiment, a "thebaine component" can include thebaine as a derivative of a chemical reaction, as detailed further in Part B, below. This term also shall be understood to encompass all dienol ether moieties in various opiates and/or opioids. For instance, oripavine, the phenolic analog of thebaine is also included under the term "thebaine component."

In one embodiment, a "composition including a thebaine component" or a "composition that includes a thebaine component" shall be understood to mean a thebaine component, as the term is defined above, either alone or in combination with additional constituents.

In one embodiment, the present invention includes a process by which a composition including a thebaine component is converted to oxycodone. In one embodiment, the process for this conversion includes the steps of:

(a) direct oxidation of a solution or a suspension composition including a thebaine component into 14-hydroxycodeinone; and (b) mild reduction of 14-hydroxycodeinone to oxycodone.

In one embodiment, the thebaine component includes CPS (Thebaine), thebaine or a salt of thebaine or mixtures thereof. In one embodiment, the conversion further includes transforming oxycodone to an acid salt of oxycodone.

Each step is described in more detail below.

Generally, and with respect to Scheme 1 below, oxycodone (III) can be prepared from thebaine (I) or its salts by oxidation to 14-hydroxycodeinone (II) followed by hydrogenation/reduction, and subsequent conversion to oxycodone, or a salt thereof (e.g., oxycodone hydrochloride).

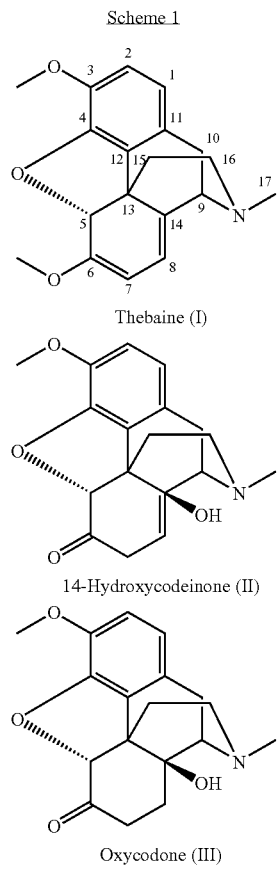

Scheme 1

Thebaine (I)

14-Hydroxycodeinone (II)

Oxycodone (III)

In one embodiment of the invention, compositions that include a thebaine component, e.g., concentrate of poppy straw enriched in thebaine (hereafter referred to as CPS (Thebaine) or CPS (T)), thebaine or its salt, is converted to oxycodone of high purity in good yield.

In one embodiment, the starting composition includes a concentrate of poppy straw. In another embodiment, a starting composition includes a concentrate of poppy straty containing about 50 to about 85 wt. % thebaine component on a wet or dry weight basis. In one embodiment, CPS (T) can contain about 50 to 99 wt. % thebaine component on a dry weight basis.

In one embodiment, CPS (T) is first isolated in the form of a thebaine salt, typically a bitartrate salt, by reacting CPS (T) with L-tartaric acid in the presence of a solvent. In one embodiment, the solvent is an alcohol, a ketone, or water, or mixtures thereof. In one embodiment, the solvent includes a $C_1-C_4$ alcohol, acetone and mixtures thereof with water. If a mixture of the $C_1-C_4$ alcohol or acetone with water is used as the solvent, the water may be present in an amount of about 5 parts to about 20 parts per 100 parts of the $C_1-C_4$ alcohol or acetone.

Accordingly, as noted above, in one embodiment of the invention, a step of a process of the present invention includes direct oxidation of a solution or a suspension containing a thebaine component such as CPS (T), thebaine or a salt of thebaine, or mixture thereof into 14-hydroxycodeinone.

1. Oxidation of CPS (Thebaine)

A. Oxidizing Agents and Conditions

In one embodiment, a composition including a thebaine component, e.g., CPS (T), is first oxidized resulting in 14-hydroxycodeinone. In certain embodiments, oxidizing conditions and reagents (i.e., an oxidizing agent) such as acid catalysts and chemical oxidants, e.g., formic acid ($HCO_2H$), m-chloroperoxybenzoic acid (MCPBA), e.g., 3-chloroperoxybenzoic acid, OXONE® (potassium peroxymonosulfate), peracids including peracetic acid (AcOOH), singlet oxygen, or iodosylbenzene can be used for oxidation of a thebaine component to 14-hydroxycodeinone. In certain embodiments, the oxidizing agents can be used alone or in combination with other suitable oxidizing agents.

In certain embodiments, a first step of the present invention includes oxidizing a composition including CPS (T) in solutions that contain one or more oxidizing agents (i.e., an oxidizing medium). Suitable solvents for use in combination with one or more oxidizing agents are discussed in more detail below in Section 1B.

In one embodiment, CPS (T) is oxidized in solutions of water, formic acid and hydrogen peroxide ($H_2O/H^+/HCO_2H/H_2O_2$); water, peracetic acid and hydrogen peroxide ($H_2O/H^+/CH_3CO_2H/H_2O_2$); methanol, formic acid and hydrogen peroxide ($MeOH/HCO_2H/H_2O_2$); or isopropyl alcohol (IPA), formic acid and hydrogen peroxide (IPA/$HCO_2H/H_2O_2$), or combinations thereof. In one embodiment, CPS (T) is oxidized in a solution that includes hydrogen peroxide in formic acid; or hydrogen peroxide in combination with one or more of an amount of acetic acid, peracetic acid, 3-chloroperoxybenzoic acid, and/or potassium peroxymonosulfate. In another embodiment, the oxidizing medium includes hydrogen peroxide in formic acid, water and isopropanol.

In general, an oxidizing agent will be utilized in an amount of about 1 to about 4.0 moles per mole of thebaine and/or thebaine salt (e.g., thebaine bitartrate) present.

In certain embodiments, the oxidation reaction temperature can be about −20–70° C., preferably about 20–50° C. In one embodiment, the temperature can be increased, either gradually or stepwise, during the reaction. The reaction proceeds at a slower rate at lower temperatures. The reactions involving acid catalysts are typically carried out at 20–25° C. whereas those in a mixture of alcohol and water are typically carried out at higher temperatures, namely at 50° C. In another embodiment, the optimum reaction time is 2–24 hours, typically in the range of about 2 to about 16 hours, preferably 2 to 15 hours.

B. Solvents for Oxidation

As suggested in Section 1A above, in certain embodiments, a solvent or solvent composition can also be used in combination with an oxidizing agent, thus forming an appropriate oxidizing medium. The solvent composition can include an acid and water, or acid and alcohol, or combinations thereof. In certain embodiments acetic acid and water; acetic acid and water and inorganic (mineral) acid; formic acid and water; formic acid and water and inorganic (mineral) acid; formic acid and methanol and water; formic acid and isopropanol; and formic acid and water and isopropanol, are included as all or part of the solvent composition.

In one embodiment, the solvent can include formic acid, acetic acid, a $C_1$–$C_4$ alcohol, water and mixtures thereof. In yet another embodiment, the oxidizing medium includes hydrogen peroxide in formic acid, water and an inorganic acid (e.g., sulfuric acid).

A preferred solvent includes about 2 to about 15, preferably 5 to 10, parts per part of CPS (T), thebaine and/or thebaine salt. The solvent can include a mixture of formic acid, water and isopropanol in a ratio of about 1.5:1.2:1. In one embodiment, a preferred solvent includes about 2 to about 15, preferably 5 to 10, parts per part of CPS (T), thebaine and/or thebaine salt, of a mixture of formic acid, water and dilute inorganic acid in a ratio of about 4:2.5:1.5.

In one embodiment, the invention directly converts a thebaine component, (e.g., CPS (T)) to 14-hydroxycodeinone of high purity (>99%) and in good yield (99%). In some embodiments, the reaction is carried out in an aqueous oxidizing medium, eliminating the need to use flammable solvents.

2. Hydrogenation of 14-hydroxycodeinone

A. Hydrogenation Agents and Conditions

In certain embodiments, conversion of 14-hydroxycodeinone produced via the reaction described above to oxycodone requires selective hydrogenation (i.e., reduction) of the double bond shown in Scheme 1, which is formed between the $C_7$ and $C_8$ atoms during the oxidation of thebaine to 14-hydroxycodeinone. It should be noted that in certain embodiments the 14-hydroxycodeinone produced in accordance with the reaction described above, does not require isolation or purification. In some embodiments, the product may be isolated in high yield if so desired.

In one embodiment, the reduction occurs in the presence of one or more of a heterogeneous catalyst, hydrogen gas, and a deactivating agent.

In certain embodiments, hydrogenation occurs over a heterogeneous metal catalyst, typically a metal catalyst from group VIII on the periodic table of elements, under the conditions set forth herein.

In one embodiment, a palladium based catalyst is the most selective catalyst to reduce a double bond in the presence of a carbonyl group. Other suitable catalysts can include catalysts such as platinum on carbon, palladium on carbon, palladium on barium sulfate ($Pd/BaSO_4$), ruthenium on carbon, and chlorotris(triphenylphosphine)rhodium ($RhCl(PPh_3)_4$).

In some embodiments, the hydrogenation catalyst will be utilized in an amount of about 0.001 to about 0.015 mole per mole of the 14-hydroxycodeinone. The hydrogenation reaction is typically carried out in a solvent that may be any of the same solvents and in the same amounts described above herein.

In one embodiment, the hydrogenation step involves mild reduction of the 14-hydroxycodeinone to oxycodone using hydrogen gas, as detailed further herein.

In one embodiment of the hydrogenation reaction described above, the hydrogen pressure is optimized. In one embodiment, hydrogenation occurs at hydrogen gas pressures up to about 55 psi, typically about 45 psi. It should be noted that lower pressures of hydrogen yield better selectivity. Accordingly, in one embodiment of the present invention, a hydrogenator can be pressurized with hydrogen gas to about 0.01 to about 20 psi, typically about 15 psi.

The hydrogenation reaction may take place in a temperature of about 0 to about 50° C., preferably 20 to 25° C. The typical reaction time is in the range of about 2 to about 36, preferably 16 to 26, hours.

B. Reduction of Catalytic Activity

In one embodiment, in order to further decrease the catalyst activity, and thus reduce the side reactions which can produce undesirable amounts of 14-hydroxydihydrocodeine, various deactivating agents can be used. In one embodiment, a hydrogenation catalyst can be used in the presence of a deactivating agent, e.g., a "catalytic poison," such as an amine or a sulfur compound to achieve high regio-selectivity. In embodiment, a lead-poisoned catalyst can be used effectively as well. In another embodiment, additives such as quinoline, quinoline-sulfur, thiourea or pyridine can be used as deactivating agents. In one embodiment, the addition of thiourea (~1 to 10 ppm aqueous solution) as a deactivating agent to the hydrogenation mixture reduces the content of 14-hydroxydihydrocodeine significantly. In certain embodiments, the level of this impurity can be reduced to 25% of its original value by the presence of a deactivating agent. In one embodiment, a preferred amount of thiourea is 1 ppm, based on the total reaction solution.

Accordingly, in one embodiment, a hydrogenation composition includes $Pd/BaSO_4$ with an amount of thiourea. The ability to control the regio-selectivity of the hydrogenation system is another salient feature of this process, which directly results in higher purity and increased yield of oxycodone.

C. Hydrogenation Solvents

It should be noted that 14-hydroxycodeinone free base is hardly soluble in water or in any organic solvent including dimethylformamide (DMF). However, 14-hydroxycodeinone free base is soluble in chlorinated solvents such as chloroform and methylene chloride. In some embodiments of the present invention, hydrogenation solvents can include organic solvents or their mixtures, and can include solvents such as ethyl acetate and chloroform; and dioxane and chloroform; and methanol and chloroform.

In one embodiment, hydrogenation solvents include a mixture of ethylene chloride and methanol. In another embodiment, 14-hydroxycodeinone can be dissolved in less than 20 parts, typically less than 10 parts of glacial acetic acid.

In another embodiment, 14-hydroxycodeinone can be dissolved in aqueous phosphate buffers at various pHs. Specifically, the starting 14-hydroxycodeinone can be dissolved in aqueous phosphate buffer at pH 1–3. However it should be noted that precipitation of 14-hydroxycodeinone typically occurs when the pH exceeds about 5.5, typically about 5.7. Accordingly, a phosphate buffer can further include a known amount of miscible organic solvents such as tetrahydrofuran (THF) and acetonitrile to keep the 14-hydroxycodeinone solubilized at higher pHs. In one embodiment, a solution of aqueous phosphate buffer (30–40 parts) and THF (5–10 parts) with a pH ~6.2 can be used to hydrogenate solubilized 14-hydroxycodeinone. Accordingly, at a higher pH the secondary reduction of the carbonyl group can be minimized.

In one embodiment, the hydrogenation solvents detailed herein can be combined together.

After the hydrogenation reaction, the catalyst can be filtered off and the aqueous filtrate can be basified with any suitable base, including ammonium hydroxide or sodium hydroxide, to afford oxycodone base as off-white to white solid precipitate.

3. Isolation of Oxycodone

In one embodiment, the solid precipitate is filtered, washed with water, and dried. In some embodiments, the resultant oxycodone base can be purified. In certain embodiments, purification occurs by isolation of oxycodone as a salt with various organic acids, including fumaric acid and tartaric acid, and/or inorganic acids such as hydrochloride. In one embodiment, the formation of oxycodone fumarate from ethanol can result in a crystalline salt with a significant purification effect. This approach is useful for the recovery and purification of oxycodone from various filtrates.

In another embodiment, the free base of oxycodone can be purified as a hydrochloride, phosphate, sulfate or acetate salt. In one embodiment, a hot suspension of oxycodone base in ethanol becomes a clear solution upon the addition of hydrochloric acid and ethanol (HCl/EtOH). Additionally, oxycodone hydrochloride is soluble in refluxing ethanol.

In one embodiment, the hot suspension is at 40–85° C. In another embodiment, the hot suspension is at 70–80° C. When cooled gradually, the product precipitates out and it is collected as off-white to white solid by filtration, washing, and drying.

In certain embodiments, the oxycodone salt is manufactured without isolating or purifying any of the intermediates produced in the course of the oxycodone production.

Accordingly, by following the steps outlined above, the typical yields for the three-step conversion is in the 50–80% range. In one embodiment, the yield can be about 70–80%.

B. Starting Compositions Including an Amount of Codeine

In one embodiment the present invention includes a process for the manufacture of oxycodone from codeine. The process can include a conversion of codeine to thebaine and thus can further include the reaction scheme set forth above for converting thebaine to oxycodone.

The process of the invention for the manufacture of oxycodone includes the following steps:

(a) converting codeine or a codeine salt into the intermediate N-carboalkoxy- or N-carboaryloxynorcodeine;

(b) oxidizing the intermediate N-carboalkoxy- or N-carboaryloxynorcodeine to yield the intermediate N-carboalkoxy- or N-carboaryloxynorcodeinone;

(c) enolizing the intermediate N-carboalkoxy- or N-carboaryloxynor-codeinone with a base and methylating the resultant enolate to yield the intermediate N-carboalkoxy- or N-carboaryloxynorthebaine;

(d) reducing the intermediate N-carboalkoxy- or N-carboaryloxynorthebaine to yield thebaine;

(e) oxidizing the thebaine to yield the intermediate 14-hydroxycodeinone; and (f) hydrogenating the intermediate 14-hydroxycodeinone to yield oxycodone.

Step (a) may be carried out by reacting the codeine or a codeine salt, e.g., codeine phosphate, with a chloroformate in the presence of an alkali metal carbonate or alkali metal bicarbonate and an inert solvent. Preferably, the chloroformate is a methyl, ethyl or phenylchloroformate. The alkali metal is typically sodium or potassium. Suitable examples of the inert solvent that may be used in step (a) include methylene chloride, chloroform, 1,2-dichloroethane and the like. Typically, the selected chloroformate will be utilized in an amount of about 1.5 to about 8.0 moles per mole of codeine or codeine salt. In general, the inert solvent will be present in the amount of about 10 to about 60, preferably 20 to 25, liters per kilogram of codeine or the selected codeine salt. The reaction involved in step (a) may be carried out at a temperature of about 0 to about 85° C., preferably 42–70° C., e.g., when the selected inert solvent is chloroform, the reaction is typically carried out under reflux at 65° C. The reaction time will typically be in the range of about 10 to about 72 hours, preferably 10 to 24 hours. The reaction in step (a) proceeds smoothly and completion of the reaction may be determined by high-pressure liquid chromatography.

Preferably, the intermediate N-carboalkoxy- or N-carboaryloxynorcodeine is not isolated, and step (b) is carried out in the same reaction vessel as employed for step (a).

Step (b) may be carried out by oxidizing the intermediate N-carboalkoxy- or N-carboaryloxynorcodeine with a suitable oxidizing agent in the presence of an inert solvent (which may be the same inert solvent as employed in step (a)). Suitable oxidizing agents include aluminum alkoxide and a ketone; a potassium alkoxide and a ketone; dimethyl sulfoxide in the presence of oxalyl chloride; manganese dioxide; potassium dichromate in the presence of sulfuric acid; and air in the presence of palladium (II) acetate. The preferred oxidizing agent comprises manganese dioxide. In general, the oxidizing agent will be used in an amount of about 7 to about 9 moles per mole of N-carboalkoxy- or N-carboaryloxynorcodeine.

Useful inert solvents for carrying out step (b) include chlorinated hydrocarbons such as chloroform, methylene chloride, 1,2-dichloroethane and the like; hydrocarbons such as benzene or toluene; esters such as ethyl acetate; and ethers such as tetrahydrofuran. The preferred solvents are chloroform and toluene. In general, the inert solvent will be utilized in an amount of about 10 to about 50, preferably 20 to 25, liters per kg of the intermediate resulting from step (a).

The oxidation reaction of step (b) may be carried out at temperatures of about 0 to about 60° C., preferably 20–25° C. Typically, the oxidation reaction for step (b) will entail a reaction time of about 6 to about 48, preferably 18 to 24, hours.

Preferably, the intermediate N-carboalkoxy- or N-carboaryloxynorcodeinone produced in step (b) is not isolated, and step (c) is carried out in the same reaction vessel as employed for step (b).

In step (c), the intermediate N-carboalkoxy- or N-carboaryloxynorcodeinone produced in step (b) is enolized using a base in an inert solvent and the resultant dienolate salt is thereafter methylated using a methylating agent. Suitable bases for carrying out the enolization reaction include sodium hydride, sodium t-butoxide, potassium t-butoxide and lithium diisopropylamide. Suitable inert solvents for carrying out the enolization reaction (and the subsequent methylation reaction) include tetrahydrofuran, N-methylpyr-rolidinone, dimethylformamide, toluene, dimethyl ether, methyl t-butyl ether, dioxane and the like.

The preferred solvent for carrying out both the enolization and the methylation reactions in step (c) comprises a mixture of about 1 part to about 20, preferably 4 parts, of tetrahydrofuran per part of N-methylpyrrolidinone. In general, the inert solvent employed in step (c) is employed in an amount of about 10 to about 50, preferably 20 to 30, liters per kg of the intermediate N-carboalkoxy- or N-carboaryloxynorcodeinone produced in step (b).

The methylation reaction may be carried out with typical methylating agents such as dimethyl sulfate, dimethyl carbonate, methyl iodide, methyl bromide, diazomethane and the like. In general, the methylating agent will be employed in an amount of about 2 to about 4 moles per mole of N-carboalkoxy- or N-carboaryloxynorcodeine.

The enolization reaction as well as the subsequent methylation reaction involved in step (c) are typically conducted at temperatures in the range of about −20 to about 50° C., preferably −5 to 5° C. The typical reaction time for carrying out both the enolization reaction as well as the methylation reaction involved in step (c) will be about 2 to about 24, preferably 8 to 15, hours.

Preferably, the intermediate N-carboalkoxy- or N-carboaryloxynorthebaine produced in step (c) is not isolated, and step (d) is carried out in the same reaction vessel as employed for step (c).

In step (d), the intermediate N-carboalkoxy- or N-carboaryloxynorthebaine is reduced to yield the intermediate thebaine. The reducing agent preferably comprises lithium aluminum hydride or sodium bis(2-methoxyethoxy)aluminum hydride (borane-tetrahydrofuran complex or borane-dimethyl sulfide complex may also be used). The reaction is generally carried out in an inert solvent such as tetrahydrofuran (which is preferred), dimethyl ether, diethyl ether, methyl t-butyl ether, and the like. Typically, such inert solvent will be utilized in an amount of 10 to about 50, preferably 20 to 30, liters per kg of the intermediate N-carboalkoxy- or N-carboaryloxynorthebaine produced in step (c).

In general, the reducing agent will be employed in step (d) in an amount of about 1 to about 3 moles per mole of N-carboalkoxy- or N-carboaryloxynorthebaine. Typically, step (d) is carried out a temperature of about 0 to about 60° C., preferably 20 to 25° C. The reaction time for carrying out the reduction reaction involved in step (d) will be about 1 to about 20, preferably 8–12, hours.

Preferably, the intermediate thebaine produced in step (d) is isolated as an acid addition salt. The isolation of the thebaine as an acid addition salt preferably involves the reaction of the thebaine with L-tartaric acid in a $C_1$–$C_4$ alcohol, acetone or a mixture thereof with water. In general, the isolation of the thebaine entails the use of about 1 to about 1.5 moles of L-tartaric acid per mole of thebaine produced in step (d). Typically, the $C_1$–$C_4$ alcohol, acetone or a mixture thereof with water will be utilized in an amount of about 5 to about 20, preferably 10–15, parts of such solvent per part of thebaine produced in step (d). If a mixture of the $C_1$–$C_4$ alcohol or acetone with water is utilized as the solvent, the water may be present in an amount of about 5 parts to about 20 parts per 100 parts of the $C_1$–$C_4$ alcohol or acetone. The preferred solvent is a mixture of methanol and water. The isolated thebaine bitartrate addition salt is recovered in a very high yield with a very high level of purity as a result of this isolation technique.

The thebaine is preferably utilized in the form of its bitartrate addition salt as the starting composition for step (e). Accordingly, in certain embodiments, steps (e) and (f) can be identical to the steps outlined above with respect to the conversion of CPS (T), thebaine or salts thereof to oxycodone.

If desired, the thebaine tartrate addition salt from step (d) may be converted to the thebaine free base (e.g., by reaction with a slight excess of a dilute aqueous base such as sodium hydroxide) and such free base may be used as the starting composition for step (e).

In step (e), the intermediate thebaine (in the form of its bitartrate addition salt or in the form of its free base) is oxidized to 14-hydroxycodeinone. For step (e), the oxidizing agent preferably comprises hydrogen peroxide, peracetic acid; m-chloroperbenzoic acid; singlet oxygen; oxone or iodosylbenzene. In general, the oxidizing agent will be utilized in an amount of about 1 to about 1.5 moles per mole of thebaine and/or thebaine salt.

Typically, the oxidation reaction of step (e) is conducted in the presence of a solvent such as formic acid, acetic acid, a $C_1$–$C_4$ alcohol, water and mixtures thereof. A preferred solvent for use in carrying out the oxidation reaction comprises about 2 to about 15, preferably 5 to 10, parts per part of thebaine and/or thebaine salt, of a mixture of formic acid, water and isopropanol in a ratio of about 1.5:1:1.

The oxidation reaction of step (e) occurs in two stages within an overall temperature range of about −20 to about 70° C., preferably 0 to 45° C. The first stage of the reaction is carried out at a cold temperature and the second stage of the reaction is carried out at a higher temperature. The reaction time for step (e) is typically in the range of about 2 to about 16, preferably 2 to 6, hours.

Preferably, the intermediate 14-hydroxycodeinone produced in step (e) is not isolated, and step (f) is carried out in the same reaction vessel as employed for step (e).

Step (f) involves the hydrogenation of the intermediate 14-hydroxycodeinone produced in step (e) to the final product oxycodone. The hydrogenation catalyst may be Raney nickel a noble metal (e.g., palladium on carbon), an oxide of a noble metal, sodium hydrosulfite and the like. The hydrogenation will be carried out at a pressure of about 15 to about 60 psi, and the hydrogenation catalyst will be utilized in an amount of about 0.001 to about 0.015 mole per mole of the 14-hydroxycodeinone. The hydrogenation reaction is typically carried out in a solvent that may be any of the same solvents and in the same amounts as indicated above for carrying out step (e).

The hydrogenation reaction involved in step (f) may take place in a temperature of about 0 to about 50° C., preferably 20 to 25° C. The typical reaction time for step (f) is in the range of about 2 to about 36, preferably 16 to 26, hours.

At the completion of step (f), the oxycodone may be isolated as a free base or a suitable acid addition salt.

The following nonlimiting examples shall serve to illustrate the preferred embodiments of the present invention. Unless otherwise indicated to the contrary, amounts and percentages are on a weight basis.

EXAMPLE 1

Preparation of 14-Hydroxycodeinone

A 0.10 L round bottom flask (RBF) is charged with 18.9 g of formic acid, 9.9 g of water, and 7.8 g of 2-propanol. This mixture is stirred at 20–30° C. for 5 minutes. Into this solution is added 5.0 g of thebaine bitartrate monohydrate. This is stirred magnetically at room temperature for 10 minutes until dissolution is achieved. The color of the solution depends on the quality of the thebaine bitartrate. Good quality of thebaine bitartrate affords a pale yellowish solution. No exothermic effect is observed. The solution is cooled in an ice-bath for 20 minutes, and then into this solution 1.29 g of hydrogen peroxide is added. The resulting solution is stirred in the ice-bath for one hour. The ice-bath is removed, and an oil-bath with temperature controller is applied to the reaction flask. Heating is started and the temperature of the reaction mixture is kept at 45° C. for 3 h (completion of reaction tested by HPLC; residual thebaine <0.5 a/a %).

The oil-bath is removed and the reaction flask is reinserted into an ice-bath and cooled for 30 minutes while it is stirred. Dropwise addition of 36.58 g of 40% NaOH solution, over a period of 20 minutes, resulted in the formation of a massive precipitate. Since the addition of base is an exothermic process, the rate of addition is controlled so that the internal temperature does not exceed 40° C. The resulting solid is continuously stirred and cooled in an ice-bath for an additional 1 h. The product is vacuum filtered using a paper filter, washed with 3×5 mL of water, and vacuum-dried for 3 h. The off-white solid of 3.05 g (93%) is obtained.

EXAMPLE 2

Preparation of Oxycodone

A known amount of THF (26.7 g) is charged into a 0.5 L RBF, and 3.05 g of 14-hydroxycodeinone is added into it. With stirring 120 g of aqueous phosphoric acid (1M, 9.8%) is added. The mixture is stirred until the entire solid dissolved. While stirring 40% aqueous sodium hydroxide is added (12.5 g) dropwise over a 30-minute period until the pH of the solution reaches 6.20–6.30. An aqueous thiourea solution (0.001% w/w, 20.0 g) is then added to the reaction flask. This buffered solution is charged into a stainless hydrogenation vessel, followed by the addition of 0.150 g of 5% palladium on barium sulfate (dry basis). The vessel is sealed, pressurized to 15 psi with nitrogen, and then ventilated. This operation is repeated 3 times with nitrogen, and then with hydrogen. The reaction vessel is finally pressurized to 15 psi with hydrogen, and is stirred at this pressure until the reaction is completed (6 hours, residual 14-hydroxycodeinone<0.5 a/a % by HPLC). The hydrogenated solution is taken out from the stainless vessel. The catalyst is vacuum filtered off through a pad of Celite. The autoclave is rinsed with water (2×5 g) and the rinses are used to wash the catalyst cake on the filter. The filtrates are combined in a 0.5 L beaker with a magnetic stirrer. The solution is cooled in an ice-bath for 30 minutes and 15.5 g of ammonium hydroxide is added dropwise over a period of 30 minutes while cooling and brisk stirring continued. The addition of aqueous ammonia is mildly exothermic, so the rate of addition should be controlled such that the temperature does not exceed 30° C. A fine white precipitate formed during the basification process. The final pH of the suspension is 10–12. The precipitate is continuously cooled and stirred for 1 hour. It is then filtered, washed with water (3×10 g), and vacuum-dried for 3 h. A white solid of oxycodone (2.80 g, 91%) is obtained.

EXAMPLE 3

Preparation of Oxycodone Hydrochloride

A known amount of oxycodone (2.80 g) is charged into a 100 mL round-bottom flask equipped with a magnetic stirrer, a reflux condenser, and a thermometer. Into this, 11 g of anhydrous ethanol is added. This is heated to reflux to form a white suspension. Into this hot suspension, 2.75 g of hydrochloride-ethanol solution (4.85 M) is added in one portion. The resulting clear solution is stirred under reflux for 30 minutes. Heating is stopped and the solution is cooled initially to room temperature, and then to 0–5° C. for 2 h. A white precipitate of oxycodone hydrochloride is formed, which is isolated by filtration. The filter cake is washed with 7.8 g of 2-propanol and vacuum-dried for 3 h to yield oxycodone hydrochloride (2.634 g, 84%) of high purity (>99.5%). The amount of final product in the mother liquor corresponded to approximately 10% yield and the purity of the same is greater than 95%.

EXAMPLE 4

Preparation of 14-Hydroxycodeinone

An 8-dram glass vial is charged with 1.425 g of concentrate of poppy straw (Anhydrous Thebaine Alkaloid=70.4% w/w), 2.323 g of water, 2.137 g of dilute sulfuric acid solution (0.4%), and 3.807 g formic acid (96%). The mixture is stirred magnetically (for a minimum of 5 minutes) until a homogenous solution is obtained. The resulting pale brown solution is cooled in an icebath for 30 minutes. A measured quantity (0.392 g) of 30% hydrogen peroxide is then added and the stirring is continued for a period of 30 minutes.

The reaction mixture is then transferred to an oilbath, heated to 50° C., and stirred until the reaction is complete (20 to 24 h). The reaction mixture is cooled to 0–5° C. and it is quenched by the addition of 7.5 ml of aqueous ammonia. A precipitate is formed and the resulting suspension is stirred for 1 h. The precipitate is filtered, washed with ice-cold water (3×10 ml), and dried under vacuum to yield an off-white solid of 14-hydroxycodeinone. The solid is recrystallized from $H_2O$-MeOH (1:3). The product formed corresponded to a yield of 74% and a purity of >99%.

EXAMPLE 5

Preparation of 14-Hydroxycodeinone

An 8-dram glass vial is charged with 1.422 g of concentrate of poppy straw (Anhydrous Thebaine Alkaloid=70.4% w/w), 2.417 g of water, 2.625 g of isopropyl alcohol, and 3.805 g formic acid (96%). The mixture is stirred magnetically (for a minimum of 5 minutes) until a homogenous solution is obtained. The resulting pale brown solution is cooled in an icebath for 30 minutes. A measured quantity (0.396 g) of 30% hydrogen peroxide is then added and the stirring is continued for a period of 30 minutes.

The reaction mixture is then transferred to an oilbath, heated to 50° C., and stirred until the reaction is complete (20 to 24 hours). The reaction mixture is cooled to 0–5° C. and it is quenched by the addition of 7.5 ml of aqueous ammonia. A precipitate is formed and the resulting suspension is stirred for 1 hour. The precipitate is filtered, washed with ice-cold water (3×10 ml), and dried under vacuum to yield an off-white solid of 14-hydroxycodeinone. The solid is recrystallized from $H_2O$-MeOH (1:3). The product formed corresponded to a yield of 83% and a purity of >99%.

EXAMPLE 6

Preparation of 14-Hydroxycodeinone

An 8-dram glass vial is charged with 1.424 g of concentrate of poppy straw (Anhydrous Thebaine Alkaloid=70.4% w/w), 2.330 g of water, 2.560 g of methanol, and 3.797 g formic acid (96%). The mixture is stirred magnetically (for a minimum of 5 minutes) until a homogenous solution is obtained. The resulting pale brown solution is cooled in an icebath for 30 minutes. A measured quantity (0.396 g) of 30% hydrogen peroxide is then added and the stirring is continued for a period of 30 minutes.

The reaction mixture is then transferred to an oilbath, heated to 50° C., and stirred until the reaction is complete (20 to 24 hours). The reaction mixture is cooled to 0–5° C. and it is quenched by the addition of 5 ml of aqueous ammonia. A precipitate is formed and the resulting suspension is stirred for 1 hour. The precipitate is filtered, washed with ice-cold water (3×10 ml), and dried under vacuum to yield an off-white solid of 14-hydroxycodeinone. The solid is recrystallized from $H_2O$-MeOH (1:3). The product formed corresponded to a yield of 65% and a purity of >99%.

EXAMPLE 7

Preparation of 14-Hydroxycodeinone

An 8-dram glass vial is charged with 1.427 g of concentrate of poppy straw (Anhydrous Thebaine Alkaloid=70.4% w/w), 2.978 g of water, 2.503 g of isopropyl alcohol, and 3.810 g formic acid (96%). The mixture is stirred magnetically (for a minimum of 5 minutes) until a homogenous solution is obtained. A measured quantity (0.563 g) of 30% hydrogen peroxide is then added and the stirring is continued for a period of 30 minutes.

The reaction mixture is then transferred to an oil bath, preheated to 50° C., and stirred until the reaction is complete (3–4 h). The reaction mixture is cooled to 0–5° C. and it is quenched by the addition of 8 ml of aqueous ammonia. A precipitate is formed and the resulting suspension is vigorously stirred for 1 h. A measured quantity (12 ml) of 25% aqueous sodium hydroxide is then added dropwise (to a pH of 12–14) and the stirring is continued in the ice-bath for an additional period of 1 h.

The precipitate is filtered, washed with ice-cold water (3×10 ml), and dried under vacuum to yield an off-white solid of 14-hydroxycodeinone. The isolated crude product corresponded to a yield of 95% and a purity of >98%. The product is recrystallized from $H_2O$—IPA (1:3). The purified product corresponded to a yield of 84% and purity greater than 99.5%. An additional 10% of 14-hydroxycodeinone (of purity>98%) may be retrieved from the mother liquor/filtrate.

EXAMPLE 8

Preparation of 14-Hydroxycodeinone

An 8-dram glass vial is charged with 1.426 g of concentrate of poppy straw (Anhydrous Thebaine Alkaloid=70.4% w/w), 2.500 g of water, 1.527 g of dilute sulfuric acid solution (0.4%), and 3.802 g formic acid (96%). The mixture is stirred magnetically (for a minimum of 5 minutes) until a homogenous solution is obtained. A measured quantity (0.522 g) of 30% hydrogen peroxide is then added and the stirring is continued at room temperature for a period of 24 h.

The reaction mixture is then transferred to an ice bath and it is quenched by the dropwise addition of 8 ml of 25% aqueous sodium hydroxide solution. A precipitate is formed at this stage (pH=5) and one more portion of the alkaline reagent (5 ml, pH=12–14) and the resulting suspension is stirred for 1 h. The precipitate is filtered, washed with ice-cold water (3×5 ml), and dried under vacuum (18 h) to yield an off-white solid of 14-hydroxycodeinone (0.989 g, 98% yield, HPLC purity of >99%).

EXAMPLE 9

Preparation of 14-Hydroxycodeinone

A 0.1 L three-neck round bottom flask is charged with 7.105 g of concentrate of poppy straw (Anhydrous Thebaine Alkaloid=70.4% w/w), 12.524 g of water, 7.500 g of dilute sulfuric acid solution (0.4%), and 19.003 g formic acid (96%). The mixture is stirred magnetically until a homogenous solution is obtained. A measured quantity (2.633 g) of 30% hydrogen peroxide is then added and the stirring is continued at room temperature for a period of 18 h.

The reaction mixture is then transferred to a 250 ml Erlenmeyer flask, cooled in an ice bath and quenched by the slow addition of 60 ml of 25% aqueous sodium hydroxide solution. A precipitate is formed and the resulting suspension is stirred for 1 h. The precipitate is filtered, repeatedly washed with ice-cold water (3×25 ml) and water/IPA (1:1, 3×20 ml), and dried under vacuum (18 h) to yield an off-white solid of 14-hydroxycodeinone (4.974 g, 99% yield, purity>98%). The solid is recrystallized from $H_2O$—IPA (1:3). The purified product is washed with ice-cold water/2-propanol (1:1, 3×20 ml) and vacuum-dried for 3 h to yield 14-hydroxycodeinone (4.277 g, 85%) of high purity (>99.5%). An additional 10% of 14-hydroxycodeinone (of purity>98%) may be recovered from the mother liquor/filtrate.

EXAMPLE 10

Preparation of N-Carboethoxynorcodeine

A 500 ml round-bottomed flask is charged with 20 g of codeine phosphate hemi-hydrate, 120 ml of chloroform, 60 ml of water and 17 ml of concentrated (28–30%) aqueous ammonia. The mixture is stirred for a minimum of 20 minutes, the stirring is stopped and the layers are allowed to separate. The bottom organic layer is separated, washed with 25 ml of water and diluted with an additional 170 ml of chloroform.

The chloroform solution is heated to reflux and dried azeotropically until no water separation is observed (3 to 5 hours). After cooling to room temperature, 8.5 g of fine anhydrous potassium carbonate is added and the reaction mixture is heated to reflux. With vigorous stirring while under reflux, a solution of 13.5 g of ethylchloroformate in 85 ml of chloroform is added to the reaction mixture over a period of 1 to 2 hours. Thereafter, the reaction mixture is stirred while under reflux until the reaction is complete, typically 6 to 12 hours.

With stirring, approximately 300 ml of solvent is distilled off under reduced pressure (e.g., 50 mm Hg). Thereafter, 330 ml of toluene is added, with stirring, to the reaction mixture and the distillation is continued until all of the chloroform has been replaced by the toluene. The reaction mixture is cooled to room temperature. The inorganic salts are filtered off and the filter cake is washed with 30 to 50 ml of toluene. The volume of the filtrate is then adjusted to a total of 305 ml with additional anhydrous toluene. The filtrate contains 16.4 g (93% yield) of the intermediate N-carboethoxynorcodeine having a purity of greater than 95% as measured by HPLC. The intermediate is an oil and the toluene solution is used in step (b) (i.e., Example 11) without purification.

EXAMPLE 11

Preparation of N-Carboethoxynorcodeinone

Manganese dioxide is added at the rate of about 8 g/hour, with vigorous stirring, to the toluene solution of the N-carboethoxynorcodeine obtained in Example 10. Typically, a total of 32–34 g of manganese dioxide is required to complete the oxidation reaction involved in step (b) of the process of the invention. The reaction time for the oxidation reaction is typically 6 to 12 hours. The manganese dioxide is filtered off and the filter cake is washed with three 40 ml portions of toluene. The filtrates are combined and the toluene solution is distilled under reduced pressure (e.g., 50 mm Hg) until the final volume has reached 34 ml. Thereafter, 180 ml of tetrahydrofuran is added to the residue. The tetrahydrofuran solution contains 15.5 g (95% yield) of N-carboethoxy-norcodeinone having a typical purity of greater than 93% as measured by HPLC. The product is an oil and is used in step (c) (i.e., Example 12) without purification.

EXAMPLE 12

Preparation of N-Carboethoxynorthebaine

Into a 500 ml round-bottomed flask is charged 14.7 g of potassium t-butoxide, 60 ml of N-methylpyrrolidinone and 60 ml of tetrahydrofuran. The mixture is stirred at room temperature for a minimum of 30 minutes and is then cooled to a temperature of 0 to 5° C. The solution obtained from Example 11 is slowly added, with stirring, while maintaining the temperature below 5° C. The reaction mixture is allowed to warm up to room temperature and is stirred at room temperature for 2 hours. The solution is then cooled to a temperature of 0 to 5° C. Thereafter, while stirring and maintaining the temperature below 5° C., 15.5 g of dimethyl sulfate is slowly added. The reaction mixture is then warmed up to room temperature and stirred at room temperature for a minimum of two hours. 60 ml of water is then added with stirring and the reaction mixture is then distilled at reduced pressure (e.g., 50 mm Hg) until the volume has reached approximately 110 ml. 60 ml of water is then added with stirring to the residue and the mixture is then extracted with two 180 ml portions of toluene. The toluene portions are combined and then washed with 15 ml of water. The solution is then dried azeotropically by heating to reflux and the toluene is distilled off until the volume of the residue is approximately 30 ml. Thereafter, 85 ml of anhydrous tetrahydrofuran is added. The tetrahydrofuran solution contains 13.7 g (85% yield) of N-carboethoxynorthebaine having a purity level of greater than 90% as measured by HPLC. The product is an oil and is used in step (d) of the process of the invention (i.e., Example 13) without purification.

EXAMPLE 13

Preparation of Thebaine Bitartrate Monohydrate

Into a 500 ml round-bottomed flask is charged 1.85 g of lithium aluminum hydride and 85 ml of anhydrous tetrahydrofuran. The suspension is vigorously stirred and the tetrahydrofuran solution of N-carboethoxynorthebaine prepared in Example 12 is slowly added. The reaction is exothermic and during the addition, the temperature is maintained below 40° C.

After completion of the addition of the tetrahydrofuran solution of N-carbo-ethoxynorthebaine, the reaction mixture is stirred at room temperature for 4 to 6 hours. Thereafter, 2.3 g of water, 2.3 g of a 15% aqueous solution of sodium hydroxide followed by 5.5 g of water are slowly added. The reaction mixture is then stirred at room temperature for 1 to 2 hours. The solids are filtered off and the filter cake is washed with three 15 ml portions of tetrahydrofuran. The tetrahydrofuran is distilled off under reduced pressure (e.g., 50 mm Hg) and is replaced with methanol, which is added in sufficient quantity to adjust the volume of the reaction mixture to 120 ml.

To the reaction mixture under reflux is added 7.1 g of L-tartaric acid in 10 ml of water. The suspension is cooled and is stirred at 0 to 5° C. for 2 to 3 hours. The solids are filtered off and the filter cake is washed with two 15 ml portions of cold methanol. After drying in vacuo (e.g., 50 mm Hg) at a temperature of 30 to 40° C., 14.5 g (82% yield) of thebaine bitartrate monohydrate is obtained. The purity level of the thebaine bitartrate monohydrate is greater than 99% as measured by HPLC. The total yield of thebaine bitartrate monohydrate based on the starting composition, i.e., codeine phosphate hemi-hydrate, is 61.5%.

EXAMPLE 14

Preparation of 14-Hydroxycodone

A 250 ml round-bottomed flask is charged with 14.5 g of the thebaine bitartrate monohydrate prepared in Example 13, 29 ml of water, 29 ml of isopropanol and 43 ml of formic acid. With stirring, the reaction mixture is cooled to 0–5° C. and 3.4 ml of 30% hydrogen peroxide are added. The mixture is stirred at 0–5° C. for 1–2 hours and thereafter is heated to 40 to 45° C. and is stirred at this temperature for 2–3 hours. The resultant solution containing 8.58 g (90% yield) of 14-hydroxycodeinone is cooled and is used in step (f) (i.e., Example 15) of the process of the invention without purification.

EXAMPLE 15

Preparation of Oxycodone

To the solution of 14-hydroxycodeinone produced in Example 14 is added 0.5 g of 5% palladium on carbon, 50% wet. The mixture is hydrogenated at 30 to 40 psi for a period of 18 to 25 hours at ambient temperature. The catalyst is filtered off and is washed with 5 ml of water. The filtrate is cooled to 0–5° C. and with stirring, sufficient concentrated (28–30%) ammonium hydroxide is added to raise the pH to 10–12. The resulting suspension is stirred at 0–5° C. for 1–2 hours. The solid is filtered off and is washed with two 5 ml portions of water. The product is dried in vacuo (e.g., 50 mm Hg) at 30–40° C. to yield 8.1 g of oxycodone (85% yield based on thebaine bitartrate). The product purity is better than 98%.

EXAMPLE 16

Preparation of Oxycodone Hydrochloride 8.1 g of oxycodone obtained in Example 15 and 80 ml of ethanol are placed in a 250 ml round-bottomed flask. The mixture is heated to reflux. Into the hot mixture is added 10 ml of a concentrated solution of hydrogen chloride in isopropanol. The mixture is cooled and stirred at 0–5° C. for 1–2 hours. The product is filtered off and the filter cake is washed with a small amount of cold ethanol. After drying in vacuo (e.g., 50 mm Hg) at 30–40° C., 7.7 g (85% yield) of pure oxycodone hydrochloride is obtained.

Although the foregoing description is directed to the preferred embodiments of the invention, it is noted that other variations and modifications in the details, materials, steps and arrangement of parts, which have been herein described and illustrated in order to explain the nature of the preferred embodiment of the invention, will be apparent to those skilled in the art, and may be made without departing from the spirit or scope of the invention.

All references referred to herein are hereby incorporated by reference in their entirety as if recited herein.

What is claimed is:

1. A process for the preparation of oxycodone, which comprises the steps of:
   (a) oxidation of a composition including a thebaine component into 14-hydroxycodeinone; and
   (b) reduction of 14-hydroxycodeinone to oxycodone;
   wherein the composition including a thebaine component comprises a concentrate of poppy straw.

2. For the preparation of an oxycodone acid salt, which comprises the steps of:
   a) oxidation of a composition including a thebaine component into 14-hydroxycodeinone;
   b) reduction of 14-hydroxycodeinone to oxycodone;
   c) transformation of the oxycodone to an acid salt.

3. The process of claim 1, wherein step (a) is carried out by reacting the thebaine component with an oxidizing agent in the presence of a solvent.

4. The process of claim 3, wherein the oxidizing agent comprises a peracid.

5. The process of claim 3, wherein the oxidizing agent of step (a) comprises hydrogen peroxide in combination with one or more of formic acid, peracetic acid, 3-chloroperoxybenzoic acid, and potassium peroxymonosulfate.

6. The process of claim 3, wherein the solvent of step (a) is selected from the group consisting of formic acid and water, formic acid and methanol and water, formic acid and isopropanol, formic acid and water and isopropanol and formic acid and water and aqueous mineral acid, acetic acid and water and aqueous mineral acid.

7. The process of claim 3, wherein the solvent comprises formic acid and water and isopropanol.

8. The process of claim 3, wherein the solvent comprises formic acid and water and aqueous sulfuric acid.

9. The process of claim 3, wherein the solvent comprises acetic acid and water and aqueous sulfuric acid.

10. The process of claim 1, wherein step (b) is carried out by reacting the 14-hydroxycodeinone intermediate in the presence of a hydrogenation solvent.

11. The process of claim 10, wherein step (b) is carried out in the presence of a heterogeneous catalyst, hydrogen gas, and a deactivating agent.

12. The process of claim 11, wherein the heterogeneous catalyst of step (b) comprises a noble metal catalyst selected from the group consisting of platinum on carbon, palladium on carbon, palladium on barium sulfate, ruthenium on carbon, and chlorotris(triphenylphosphine)rhodium.

13. The process of claim 11, wherein the deactivating agent of step (b) is selected from the group consisting of thiourea and pyridine.

14. The process of claim 10, wherein the hydrogenation solvent of step (b) is selected from the group consisting of ethyl acetate and chloroform; dioxane and chloroform; methanol and chloroform; and aqueous phosphate buffer and tetrahydrofuran.

15. The process of claim 2, wherein the oxycodone is isolated in the form of its hydrochloride salt by reacting the oxycodone with hydrochloric acid or hydrogen chloride gas in the presence of a solvent selected from the group consisting of a C1–C4 alcohol, acetone and mixtures thereof with water.

16. The process of claim 1, wherein the concentrate of poppy straw comprises a concentrate of poppy straw having a thebaine content of about 30 to 83 wt.%.

17. The process of claim 2, wherein the acid salt is selected from the group consisting of phosphate, hydrochloride, sulfate and acetate.

18. The process of claim 1, wherein the 14-hydroxycodeinone or its salt produced in step (a) is utilized in step (b) without isolation or purification.

19. The process of claim 2, wherein the oxycodone produced in step (b) is transformed to the salt in step (c), without isolation or purification.

20. The process of claim 2, wherein the oxycodone salt is manufactured without isolating or purifying any of the intermediates produced in the course of steps (a) and (b).

21. The process of claim 1, wherein a thebaine salt is isolated from the concentrated poppy straw by reacting concentrated poppy straw with an acid in the presence of a solvent selected from the group consisting of an alcohol, a ketone and mixtures thereof, before step (a), wherein the thebaine salt is oxidized in step (a).

* * * * *